United States Patent
Ha et al.

(10) Patent No.: US 9,090,830 B2
(45) Date of Patent: Jul. 28, 2015

(54) METHOD OF MANUFACTURING HIGH-CARBON NUMBER SATURATED HYDROCARBONS FROM BIOMASS-DERIVED BENZYL PHENYL ETHERS USING ACID-METAL COMPLEX CATALYST

(71) Applicant: KOREA INSTITUTE OF SCIENCE AND TECHNOLOGY, Seoul (KR)

(72) Inventors: Jeong-Myeong Ha, Seoul (KR); Jae Wook Choi, Incheon (KR); Dong Jin Suh, Seoul (KR); Young Hyun Yoon, Seoul (KR); Ji Sun Yoon, Seoul (KR); Gi Seok Yang, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 281 days.

(21) Appl. No.: 13/864,371

(22) Filed: Apr. 17, 2013

(65) Prior Publication Data

US 2014/0179966 A1  Jun. 26, 2014

(30) Foreign Application Priority Data

Dec. 20, 2012 (KR) .......... 10-2012-0149171

(51) Int. Cl.
  *C07C 1/24* (2006.01)
  *C10G 3/00* (2006.01)
  *C07C 1/22* (2006.01)
  *C07C 37/055* (2006.01)

(52) U.S. Cl.
  CPC ... *C10G 3/00* (2013.01); *C07C 1/22* (2013.01); *C07C 37/055* (2013.01); *C07C 2101/14* (2013.01); *C07C 2521/02* (2013.01); *C07C 2521/06* (2013.01); *C07C 2523/04* (2013.01)

(58) Field of Classification Search
  USPC .................................. 585/240, 733
  See application file for complete search history.

(56) References Cited

U.S. PATENT DOCUMENTS

| | | | |
|---|---|---|---|
| 4,117,243 A * | 9/1978 | Starks et al. | 568/744 |
| 2012/0156109 A1 | 6/2012 | Parimi et al. | |
| 2012/0238792 A1 | 9/2012 | Watson et al. | |

FOREIGN PATENT DOCUMENTS

| | | |
|---|---|---|
| KR | 1020040094763 A | 11/2004 |
| KR | 1020100059398 A | 6/2010 |
| KR | 20110094204 A | 8/2011 |
| KR | 20120104520 A | 9/2012 |
| KR | 101189818 B1 | 10/2012 |
| WO | 2010/065643 A2 | 6/2010 |
| WO | 2011/031320 A2 | 3/2011 |

OTHER PUBLICATIONS

Mahesh H. Bhure, et al; "Phosphotungstic acid as an efficent solid catalyst for intramolecular rearrangement of benzyl phenyl ether to 2-benzyl phenol", Catalysis Communications 8, Issue 2, pp. 139-144; Feb. 2007.

* cited by examiner

*Primary Examiner* — Thuan D Dang
(74) *Attorney, Agent, or Firm* — Ladas & Parry LLP (57) ABSTRACT

Provided is a method for producing a high-carbon number saturated hydrocarbon compound by subjecting a mixed biomass solution containing benzyl phenyl ether ($C_6H_5CH_2OC_6H_5$) to a two-step reaction process using a difunctional catalyst having an acid catalyst combined with a metal catalyst. The method allows development of a fuel substituting for and supplementing petroleum through decomposition and conversion of a biomass containing lignin or the like, thereby providing a non-petroleum based biofuel.

12 Claims, 5 Drawing Sheets

FIG. 1

FIG. 2 benzyl phenyl ether 2-benzylphenol 4-benzylphenol phenol dicyclohexylmethane cyclohexane methylcyclohexane cycloheptane methylcyclopentane

METHOD OF MANUFACTURING HIGH-CARBON NUMBER SATURATED HYDROCARBONS FROM BIOMASS-DERIVED BENZYL PHENYL ETHERS USING ACID-METAL COMPLEX CATALYST

CROSS-REFERENCE TO RELATED APPLICATION

This application claims priority to Korean Patent Application No. 10-2012-0149171, filed on Dec. 20, 2012, and all the benefits accruing therefrom under 35 U.S.C. §119, the contents of which in its entirety are herein incorporated by reference.

BACKGROUND

1. Field

The present disclosure relates to a method for producing a saturated hydrocarbon fuel that may be used as diesel and aerial oil by subjecting a biomass containing benzyl phenyl ether to isomerization and hydrodeoxygenation using an acid-metal composite catalyst. More particularly, the present disclosure relates to a method for producing a high-carbon number saturated hydrocarbon fuel by isomerizing the oxygen present in benzyl phenyl ether derived from lignin as a biomass into an aromatic alcohol, while inhibiting decomposition of a carbon compound.

2. Description of the Related Art

Lignocellulosic biomass occupying 95% or more of the total vegetable biomasses includes cellulose (40-60%), hemicellulose (20-40%) and lignin (10-25%). Cellulose and hemicellulose have been studied intensively about production of bioethanol through saccharification and fermentation processes. However, lignin forms a natural polymer structure of complicated phenolic compounds to serve to protect vegetable cells from external biological attacks, and thus forms a rigid cellular wall.

Since it is difficult to decompose lignin as mentioned above, it is frequently discarded, or it largely depends on a thermal decomposition process requiring high energy consumption using high temperature and pressure, if it may be utilized as a fuel or chemical product. In brief, there are only insufficient technological processes for converting lignin into an energy source capable of substituting for the existing petrochemicals. Bio-oil obtained through thermal decomposition of lignin has a large amount of water and oxygen functional groups, and thus is problematic in that it easily causes corrosion of metals, or the like. Therefore, such bio-oil has many potential problems in terms of corrosion of engines when used as a fuel for vehicles.

Accordingly, there is an imminent need for developing a process for converting lignin efficiently into one that may be used as a high-energy source. Benzyl phenyl ether is a typical compound derived from lignin and includes two benzene rings and ether bond, so that it represents characteristics of lignin decomposition materials. Conversion of benzyl phenyl ether may be applied to conversion of other lignin-derived compounds.

Use of lignin as a biofuel is intended to minimize the number of oxygen functional groups present in lignin, and thus to minimize thermal and chemical unstability of biofuel, thereby providing a high-efficiency energy source. In addition, a particular process thereof includes an indirect hydrodeoxygenation process in which hydrodeoxygenation is accomplished while maintaining a high carbon number of starting materials through isomerization, instead of cleavage of an ether functional group that is a kind of oxygen functional group present in high-molecular weight lignin structure to produce low-molecular weight carbon compounds.

The present inventors have developed a two-step process including: isomerization of lignin dimer having an ether functional group (($C_nH_m$)—O—($C_xH_y$)) for conversion into an optimized biofuel having highly efficient quality; and hydrodeoxygenation. We also have developed an optimized acid catalyst for the isomerization and an optimized composite of metal nanoparticles with an acid catalyst for the hydrodeoxygenation.

REFERENCES OF THE RELATED ART

Patent Document (Patent Document 1) Korean Patent Publication No. 10-1189818
(Patent Document 2) Korean Patent Publication No. 10-2004-0094763

SUMMARY

The present disclosure is directed to providing a method for producing a high-carbon number saturated hydrocarbon compound that has a carbon number of 13-19 and may be used as fuel such as aerial oil or diesel by using a biomass containing benzyl phenyl ether ($C_6H_5CH_2OC_6H_5$) as a starting material, and by inducing isomerization and indirect hydrodeoxygenation through a two-step process using an acid catalyst or a difunctional catalyst having the acid catalyst combined with a metal catalyst.

In one aspect, there is provided a method for producing a high-carbon number saturated hydrocarbon using a biomass, including: introducing a mixed biomass solution containing benzyl phenyl ether ($C_6H_5CH_2OC_6H_5$) to a reactor and further introducing an acid catalyst or difunctional catalyst to the reactor to carry out isomerization of the mixed biomass solution; and carrying out hydrodeoxygenation by introducing an acid catalyst or difunctional catalyst to the reactor together with hydrogen, after the isomerization, to induce hydrodeoxygenation of intermediate products obtained from the isomerization.

According to an embodiment, the mixed biomass solution may include the biomass containing benzyl phenyl ether, dissolved in at least one hydrocarbon solvent selected from the group consisting of pentane, hexane, heptane, octane, nonane, decane, undecane and dodecane.

According to another embodiment, benzyl phenyl ether may be present in the mixed biomass solution in an amount of 0.1-10 wt % based on the total weight of the solution.

According to still another embodiment, the acid catalyst may include a porous or non-porous carrier having acidic functional groups on the surface thereof.

According to still another embodiment, the carrier of the acid catalyst may be at least one selected from the group consisting of aluminum, silicon and silicon-aluminum mixed oxide.

According to still another embodiment, the carrier of the acid catalyst may be silicon-aluminum mixed oxide, wherein the ratio of aluminum/(silicon+aluminum) in the mixed oxide may be 0.1-100.

According to still another embodiment, the acid catalyst may have at least one shape selected from the group consisting of bulk, plates, powder, pellets, balls and aerogel.

According to still another embodiment, the metal catalyst contained in the difunctional catalyst may be a metal nanoparticle catalyst.

According to still another embodiment, the metal may be at least one metal selected from the group consisting of platinum, palladium, rubidium, iridium and rhodium or alloy thereof.

According to still another embodiment, the metal catalyst contained in the difunctional catalyst may be supported in an amount of 0.1-20 wt % based on the weight of the carrier.

According to still another embodiment, the reactor may be maintained at a temperature of 50-150° C. during the isomerization.

According to yet another embodiment, the reactor may be maintained at a temperature of 200-300° C. during the hydrodeoxygenation.

The method disclosed herein may be applied to development of a fuel substituting for petroleum through decomposition and conversion of a biomass containing lignin or the like, thereby substituting for or supplementing the conventional method for producing a high-carbon number saturated hydrocarbon in the field of petrochemical industry.

The method disclosed herein allows production of a high-carbon number saturated hydrocarbon with high efficiency.

BRIEF DESCRIPTION OF THE DRAWINGS

The above and other aspects, features and advantages of the disclosed exemplary embodiments will be more apparent from the following detailed description taken in conjunction with the accompanying drawings in which.

[Detailed Description of Main Elements]

10: gas mixing valve  11: high-pressure helium cylinder
12: high-pressure hydrogen cylinder  13: vacuum pump
20: cooling tube  21: gas phase product collector
30: high-pressure reactor  31: agitation impeller
40: thermometer  50: pressure meter
60: temperature and agitation speed controller
70: computer for storing temperature/pressure/agitation speed measurement results
80: liquid phase product collector

DETAILED DESCRIPTION

Exemplary embodiments now will be described more fully hereinafter with reference to the accompanying drawings, in which exemplary embodiments are shown.

In one aspect, there is provided a method for producing a high-carbon number saturated hydrocarbon compound with high efficiency by adding an acid catalyst or difunctional catalyst having the acid catalyst combined with a metal catalyst to a biomass containing benzyl phenyl ether ($C_6H_5CH_2OC_6H_5$).

As used herein, the term 'hydrodeoxygenation' means a reaction in which hydrogen is added to remove oxygen.

As used herein, the term 'difunctional catalyst' means a catalyst having components with two functions, and particularly refers to a catalyst having an acid catalyst combined or mixed with a metal catalyst herein.

According to an embodiment, the method for producing a high-carbon number saturated hydrocarbon using a biomass includes: introducing a mixed biomass solution containing benzyl phenyl ether ($C_6H_5CH_2OC_6H_5$) to a reactor, and further introducing an acid catalyst or difunctional catalyst to the reactor to carry out isomerization of the mixed biomass solution; and carrying out hydrodeoxygenation by introducing an acid catalyst or difunctional catalyst to the reactor together with hydrogen, after the isomerization, to induce hydrodeoxygenation of intermediate products obtained from the isomerization.

Although there is no particular limitation in the reactor, a batch type high-temperature high-pressure reactor resisting against high temperature and high pressure may be used in accordance with an exemplary embodiment.

The reactor may be heated to 50-150° C. during the isomerization, and to 200-300° C. during the hydrodeoxygenation.

Particularly, according to the method disclosed herein, the two-step process including the isomerization and hydrodeoxygenation enables highly efficient production of a high-carbon number saturated hydrocarbon compound from a biomass starting material containing lignin or the like, so that the resultant compound may substitute for a petroleum source.

More particularly, according to an embodiment, a mixed biomass solution containing benzyl phenyl ether ($C_6H_5CH_2OC_6H_5$) is introduced to a reactor first, and then an acid catalyst or difunctional catalyst is introduced thereto to carry out isomerization of the mixed biomass solution.

Figure 1:
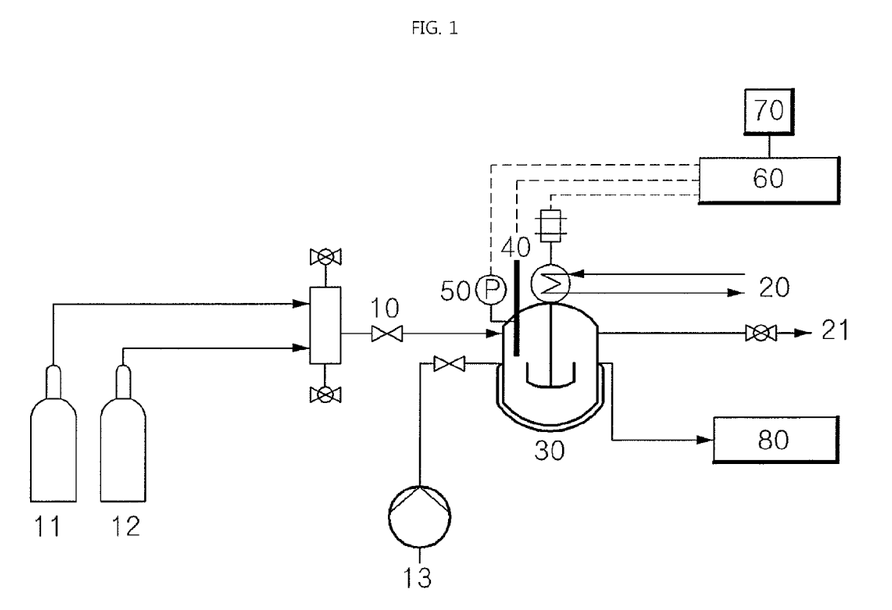
FIG. 1 shows a high-temperature high-pressure reactor in which isomerization and hydrodeoxygenation are carried out to produce a hydrocarbon in accordance with an embodiment.

When carrying out the isomerization, the inner part of the reactor is filled with another gas to maintain an adequate pressure inside the reactor. The filling gas may be inert gas, such as hydrogen, helium or nitrogen, but is not limited thereto. Particularly, the inner part of the reactor may be filled with such inert gas to maintain an adequate pressure inside the reactor. The reactor may have an internal pressure of 1-100 bar, particularly 5-50 bar during the isomerization. The internal pressure of the reactor is measured by a pressure gauge 50 attached to the reactor.

When carrying out the isomerization, the reactor may be heated to a temperature of 50-150° C. Particularly, the reactor may be heated to a temperature around 100° C. suitable for the isomerization and maintained at this temperature constantly during the reaction. For this, when carrying out the isomerization, the reactor may be heated at a constant heating rate of 2-10° C. per minute, particularly 3° C. per minute.

The isomerization may be performed as an isothermal reaction at a desired temperature around 100° C. for 0-100 hours, particularly for about 1 hour. The isomerization may be carried out with agitation to facilitate the reaction. Particularly, to perform such agitation, an agitation impeller 31 attached to the reactor may be operated at 200-1200 rpm, particularly at 1000 rpm to carry out mixing. With regard to the agitation speed during the reaction, variations in speed and controlling conditions of speed are stored in a computer 70 through an agitation speed controller 60 in a real time mode.

After the reaction, the method may further include cooling the reactor. The cooling operation may be carried out by introducing a cooling fluid to the reactor.

The mixed biomass solution containing benzyl phenyl ether ($C_6H_5CH_2OC_6H_5$) may be obtained by dissolving a biomass containing benzyl phenyl ether ($C_6H_5CH_2OC_6H_5$) into at least one hydrocarbon solvent selected from the group consisting of pentane, hexane, heptane, octane, nonane, decane, undecane and dodecane.

Particularly, the biomass may include cellulose, hemicellulose or lignin forming a lignocellulosic biomass. More particularly, the biomass may be lignin dimer containing benzyl phenyl ether.

According to an embodiment, benzyl phenyl ether may be present in an amount of 0.1-10 wt % based on the total weight of the mixed solution, due to a limitation in benzyl phenyl ether solubility.

To accelerate the isomerization of the mixed biomass solution, an acid catalyst or difunctional catalyst may be used and introduced to the reactor.

The acid catalyst may include a porous or non-porous carrier having acidic functional groups on the surface thereof, and the acidic functional groups are not particularly limited. For example, the acidic functional group may be a hydroxyl group, such as Si—OH or Al—OH, a carboxyl group or a cationic metal atom exposed to the catalyst surface.

There is no particular limitation in the carrier of the acid catalyst. For example, the carrier may be at least one selected from the group consisting of aluminum, silicon and silicon-aluminum mixed oxide. When the carrier of the acid catalyst is silicon-aluminum mixed oxide, the atomic ratio between silicon and aluminum (Al/(Si+Al)) may be 0.1-100. Herein, a change in the atomic ratio results in a change in property and number of the acidic functional groups.

There is no particular limitation in shape of the acid catalyst. In general, the acid catalyst may have at least one shape selected from the group consisting of bulk, plates, powder, pellets, balls and aerogel.

The difunctional catalyst is a catalyst including the acid catalyst combined with a metal catalyst. The metal catalyst may be present in the difunctional catalyst in an amount of 0.01-10 wt % based on the total weight of the catalyst. When the metal content is less than 0.01 wt %, it is not possible to carry out hydrodeoxygenation sufficiently. On the other hand, when the metal content is greater than 10 wt %, it is not favorable in view of cost efficiency.

There is no particular limitation in the metal catalyst present in the difunctional catalyst. For example, the metal catalyst may be a metal nanoparticle catalyst.

Particularly, the metal may be a noble metal or transition metal. More particularly, the metal may be at least one metal selected from the group consisting of platinum (Pt), palladium (Pd), rubidium (Ru), iridium (Ir) and rhodium (Rh) or alloy thereof.

The metal catalyst contained in the difunctional catalyst may be supported in an amount of 0.1-20 wt % based on the weight of the carrier. Particularly, the metal catalyst may be supported in an amount of 0.1-10 wt % based on the weight of the carrier. When the metal catalyst is supported in an amount less than 0.1 wt %, the catalyst content is too insufficient to obtain catalytic activity, resulting in a drop in reaction yield. On the other hand, when the metal catalyst is supported in an amount greater than 20 wt %, there is a waste of catalyst with no additional benefit.

Figure 2:
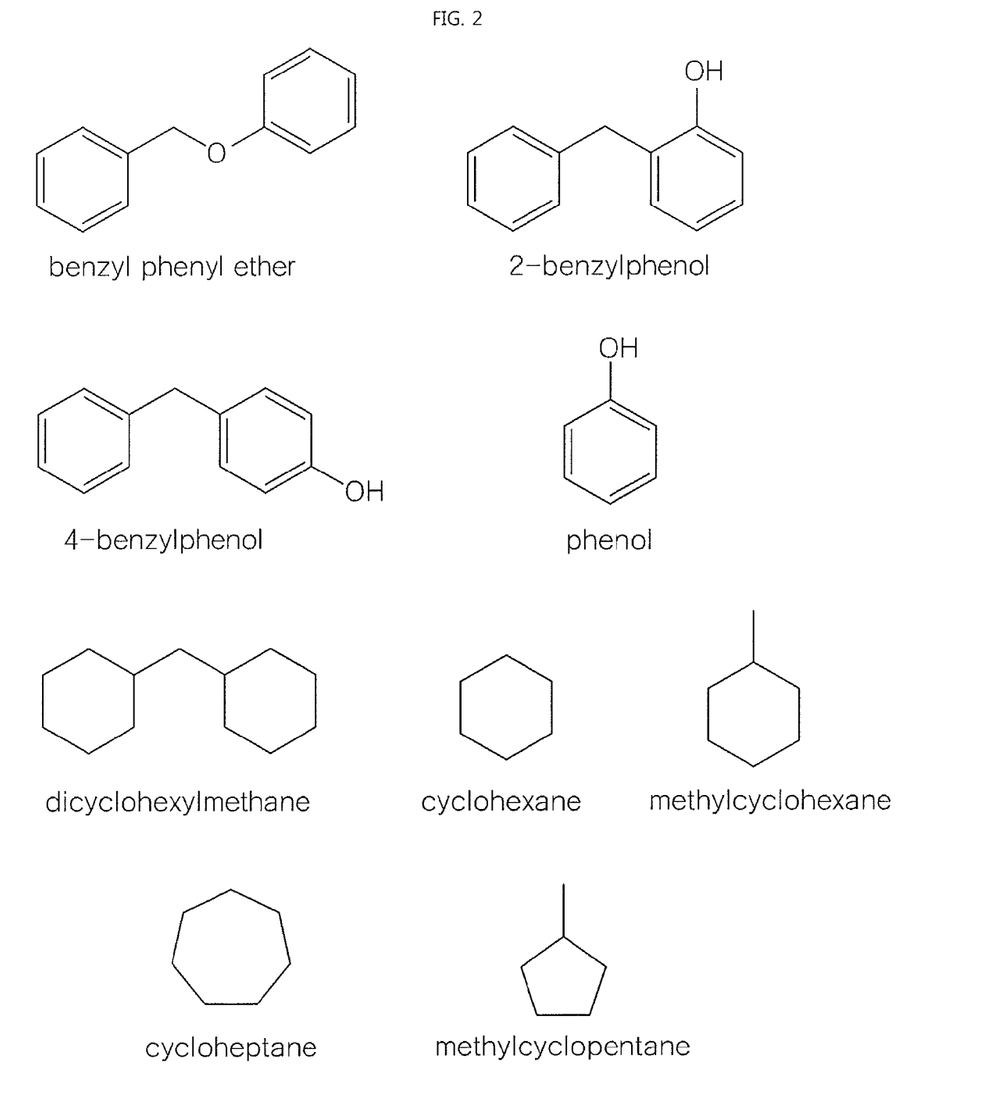
FIG. 2 shows the chemical molecular structures of benzyl phenyl ether ($C_6H_5CH_2OC_6H_5$), intermediate products obtained from benzyl phenyl ether ($C_6H_5CH_2OC_6H_5$) via isomerization, final products obtained from the intermediate products via hydrodeoxygenation and byproducts, in accordance with an embodiment.

After the isomerization, intermediate products are produced and the particular types of the intermediate products depend on the mixed biomass solution. For example, the intermediate products may be 2-benzylphenol, 4-benzylphenol or phenol (see FIG. 2).

After the intermediate products are obtained from the isomerization, an acid catalyst or difunctional catalyst is introduced to the reactor, in which the intermediate products have been produced, together with hydrogen. In this manner, the intermediate products are subjected to hydrodeoxygenation. After the completion of hydrodeoxygenation, a high-carbon number saturated hydrocarbon is obtained as a final product.

When carrying out the hydrodeoxygenation, the inner part of the reactor is filled with hydrogen gas that serves as a reactant while maintaining an adequate internal pressure of the reactor. The internal pressure of the reactor may be 1-100 bar, particularly 5-50 bar. The pressure is measured by a pressure gauge 50 attached to the reactor.

When carrying out the hydrodeoxygenation, the reactor may be heated to a temperature of 200-300° C. Particularly, the reactor may be heated to a temperature around 250° C. suitable for the hydrodeoxygenation and maintained at this temperature constantly during the reaction. For this, when carrying out the hydrodeoxygenation, the reactor may be heated at a constant heating rate of 2-10° C. per minute, particularly 7° C. per minute.

The hydrodeoxygenation may be performed as an isothermal reaction at a desired temperature around 250° C. for 0-10 hours, particularly for about 1 hour. The hydrodeoxygenation may be carried out with agitation to facilitate the reaction. Particularly, to perform such agitation, an agitation impeller 31 attached to the reactor may be operated at 200-1200 rpm, particularly at 1000 rpm to carry out mixing. With regard to the agitation speed during the reaction, variations in speed and controlling conditions of speed are stored in a computer 70 through an agitation speed controller 60 in a real time mode.

After the reaction, the method may further include cooling the reactor. The cooling operation may be carried out by introducing a cooling fluid to the reactor.

The acid catalyst or difunctional catalyst introduced during the hydrodeoxygenation may be the same as or different from the acid catalyst or difunctional catalyst introduced during the isomerization. In addition, an acid catalyst may be used in the hydrodeoxygenation. However, when using a difunctional catalyst including an acid catalyst combined with a metal catalyst, it is possible to obtain higher reaction efficiency.

The acid catalyst may include a porous or non-porous carrier having acidic functional groups on the surface thereof, and the acidic functional groups are not particularly limited. For example, the acidic functional group may be a hydroxyl group, such as Si—OH or Al—OH, a carboxyl group or a cationic metal atom exposed to the catalyst surface.

There is no particular limitation in the carrier of the acid catalyst. For example, the carrier may be at least one selected from the group consisting of aluminum, silicon and silicon-aluminum mixed oxide. When the carrier of the acid catalyst is silicon-aluminum mixed oxide, the atomic ratio between silicon and aluminum (Al/(Si+Al)) may be 0.1-100. Herein, a change in the atomic ratio results in a change in property and number of the acidic functional groups.

There is no particular limitation in shape of the acid catalyst. In general, the acid catalyst may have at least one shape selected from the group consisting of bulk, plates, powder, pellets, balls and aerogel.

The difunctional catalyst is a catalyst including the acid catalyst combined with a metal catalyst. The metal catalyst may be present in the difunctional catalyst in an amount of 0.01-10 wt % based on the total weight of the catalyst. When the metal content is less than 0.01 wt %, it is not possible to carry out hydrodeoxygenation sufficiently. On the other hand, when the metal content is greater than 10 wt %, it is not favorable in view of cost efficiency.

There is no particular limitation in the metal catalyst present in the difunctional catalyst. For example, the metal catalyst may be a metal nanoparticle catalyst.

Particularly, the metal may be a noble metal or transition metal. More particularly, the metal may be at least one metal selected from the group consisting of platinum (Pt), palladium (Pd), rubidium (Ru), iridium (Ir) and rhodium (Rh) or alloy thereof.

The metal catalyst contained in the difunctional catalyst may be supported in an amount of 0.1-20 wt % based on the weight of the carrier. Particularly, the metal catalyst may be supported in an amount of 0.1-10 wt % based on the weight of the carrier. When the metal catalyst is supported in an amount less than 0.1 wt %, the catalyst content is too insufficient to obtain catalytic activity, resulting in a drop in reaction yield. On the other hand, when the metal catalyst is supported in an amount greater than 20 wt %, there is a waste of catalyst with no additional benefit.

After the completion of the hydrodeoxygenation, a high-carbon number saturated hydrocarbon is produced as a final product. The final product may depend on the initially introduced mixed biomass solution. For example, the final product may be dicyclohexylmethane, cyclohexane, methylcyclohexane, cycloheptane or methylcyclopentane (see FIG. 2).

Particularly, the reactor may be heated to a temperature of 50-150° C. during the isomerization, while the reactor may be heated to a temperature of 200-300° C. during the hydrodeoxygenation.

The isomerization and hydrodeoxygenation carried out sequentially in the reactor may further include, after each operation is completed, collecting the product produced in the reactor and analyzing the product. For such collecting and analyzing operations, a collecting tube 21, gas chromatography and gas chromatography-mass spectrometer may be used.

EXAMPLES

The examples and experiments will now be described. The following examples and experiments are for illustrative purposes only and not intended to limit the scope of the present disclosure.

Example 1

The system as shown in FIG. 1 is used to carry out a two-step reaction process for converting benzyl phenyl ether into a saturated hydrocarbon in a liquid phase at high temperature under high pressure.

Figure 3:
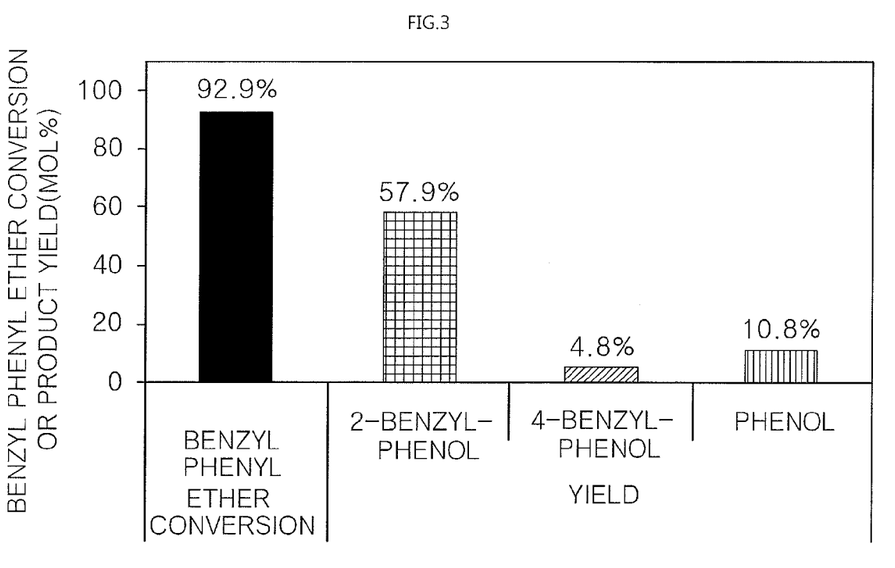
FIG. 3 is a graph illustrating the yields of the intermediate products obtained from benzyl phenyl ether ($C_6H_5CH_2OC_6H_5$) via isomerization according to Example 1.

To carry out isomerization, as a reaction mixture, 40 mL of a solution containing 1 wt % of benzyl phenyl ether dissolved in n-decane ($C_{10}H_{22}$) is introduced to a high-temperature high-pressure reactor 30. In addition, 0.1 g of 2 wt % rubidium/silicon-aluminum mixed oxide is introduced to the reactor as a difunctional catalyst. To remove oxygen in the reactor, helium is introduced at room temperature under ambient pressure, and then removed by a vacuum pump 13. This operation is repeated three times. Then, hydrogen is introduced at room temperature under ambient pressure, and then removed by a vacuum pump 13. This operation is repeated twice. A pressure gauge 50 is used to determine that injection of hydrogen into the reactor allows the internal pressure of the reactor to reach 5 bars. At this time, all valves connected to the reactor are interrupted so that the inner part of the reactor is sealed tightly. An impeller 31 and an agitation speed controller 60 are used to control the agitation speed to 1000 rpm. The heater attached to the reactor 30 is operated and a reaction temperature controller 60 is used to adjust the reaction temperature in the reactor to 100° C. The reactor 30 is heated at a heating rate of 3° C. per minute so that it reaches to a reaction temperature of 100° C. The temperature of the reactor 30 is controlled by the heater attached to the reactor and cooling water as a cooling fluid supplied through a cooling tube 20 connected to the reactor. The reaction temperature is maintained so that the reaction is carried out for 1 hour. After the lapse of a predetermined reaction time, the heater attached to the reactor 30 is stopped and cooling water is allowed to flow so that the temperature of the reactor decreases to room temperature. Then, gas phase products are collected with a gas phase collector 21, and liquid phase products are collected with a liquid phase collector 80. Subsequently, the products are analyzed in their composition by gas chromatography and gas chromatography-mass spectrometry. The results of the liquid phase mixture are shown in FIG. 3.

Example 2

Figure 6:
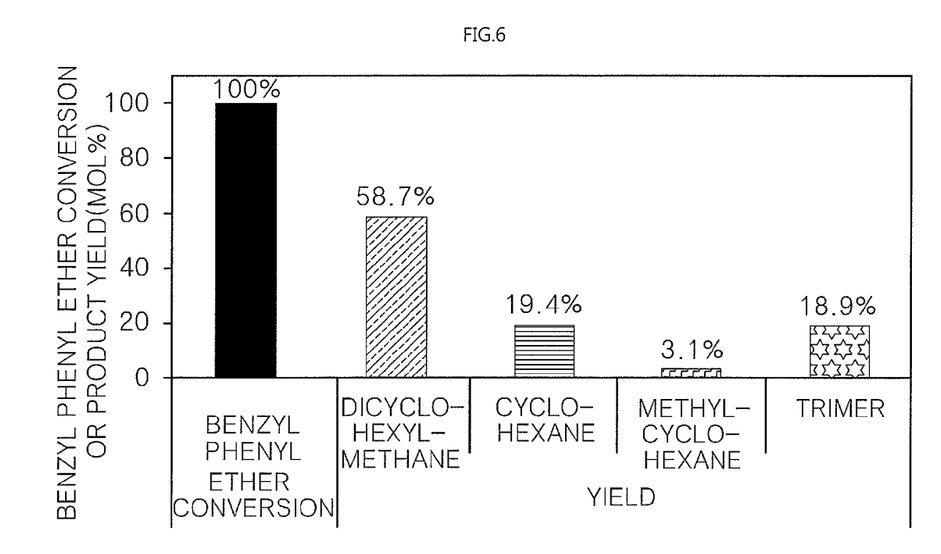
FIG. 6 is a graph illustrating the yields of the final products obtained from the intermediate products and byproducts as shown in FIG. 3 via hydrodeoxygenation according to Example 2.

To carry out hydrodeoxygenation, 0.1 g of 2 wt % rubidium/silicon-aluminum mixed oxide as a difunctional catalyst is introduced to the products obtained from the isomerization according to Example 1 in the reactor. To remove oxygen in the reactor 30, helium is introduced at room temperature under ambient pressure, and then removed by a vacuum pump 13. This operation is repeated three times. Then, hydrogen is introduced at room temperature under ambient pressure, and then removed by a vacuum pump 13. This operation is repeated twice. A pressure gauge 50 is used to determine that injection of hydrogen into the reactor allows the internal pressure of the reactor to reach 40 bars. At this time, all valves connected to the reactor are interrupted so that the inner part of the reactor is sealed tightly. An impeller 31 and an agitation speed controller 60 are used to control the agitation speed to 1000 rpm. The heater attached to the reactor 30 is operated and a reaction temperature controller 60 is used to adjust the reaction temperature in the reactor to 250° C. The reactor 30 is heated at a heating rate of 7° C. per minute so that it reaches to a reaction temperature of 250° C. The temperature of the reactor 30 is controlled by the heater attached to the reactor and cooling water as a cooling fluid supplied through a cooling tube 20 connected to the reactor. The reaction temperature is maintained constantly so that the reaction is carried out for 1 hour. After the lapse of a predetermined reaction time, the heater attached to the reactor 30 is stopped and cooling water is allowed to flow so that the temperature of the reactor decreases to room temperature. Then, gas phase products are collected with a gas phase collector 21, and liquid phase products are collected with a liquid phase collector 80. Subsequently, the products are analyzed in their composition by gas chromatography and gas chromatography-mass spectrometry. The results are shown in FIG. 6.

Comparative Example 1

Figure 4:
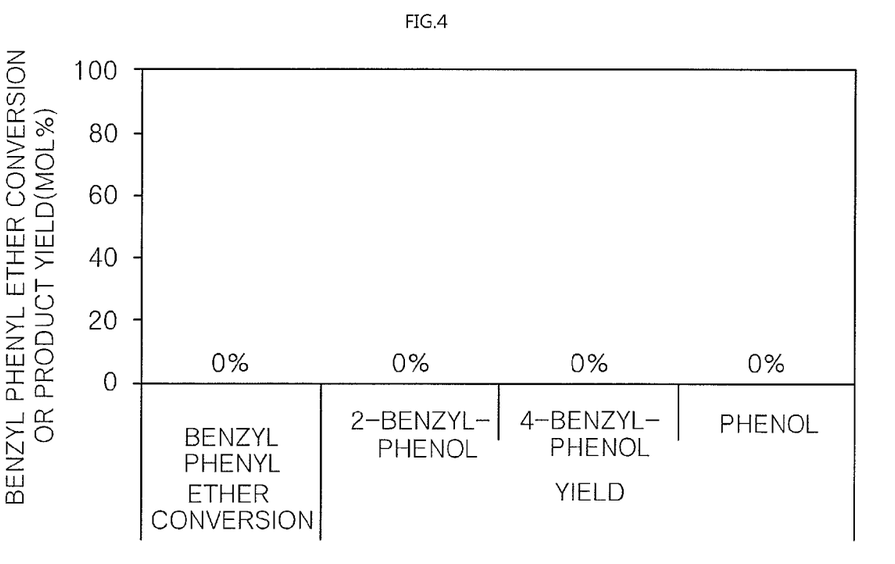
FIG. 4 is a graph illustrating the yields of the intermediate products obtained from benzyl phenyl ether ($C_6H_5CH_2OC_6H_5$) via isomerization according to Comparative Example 1.

Example 1 is repeated, except that no catalyst is introduced. The results are shown in FIG. 4.

Comparative Example 2

Figure 5:
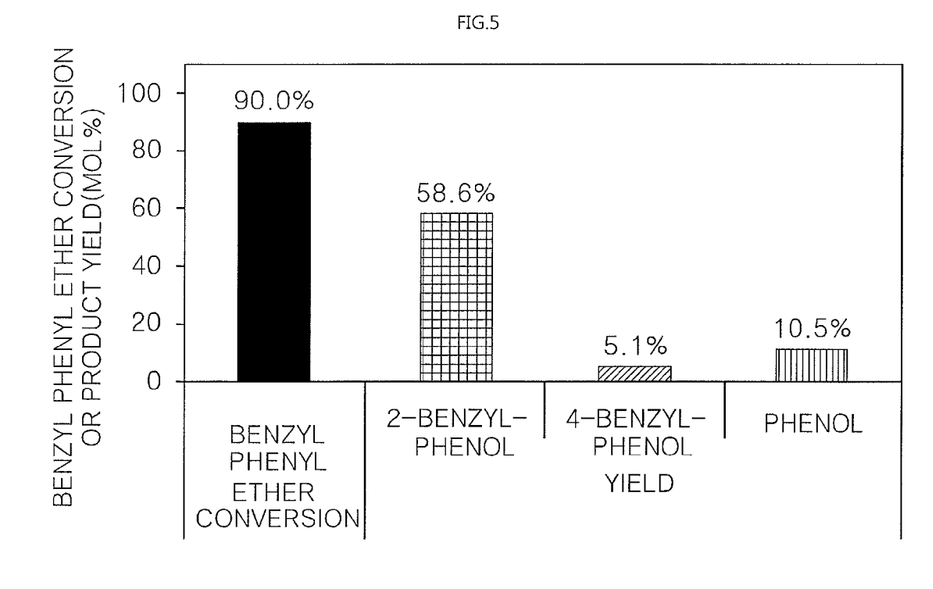
FIG. 5 is a graph illustrating the yields of the intermediate products obtained from benzyl phenyl ether ($C_6H_5CH_2OC_6H_5$) via isomerization according to Comparative Example 2.

Example 1 is repeated, except that helium is introduced to the reactor for the reaction instead of hydrogen. The results are shown in FIG. 5.

Comparative Example 3

Figure 7:
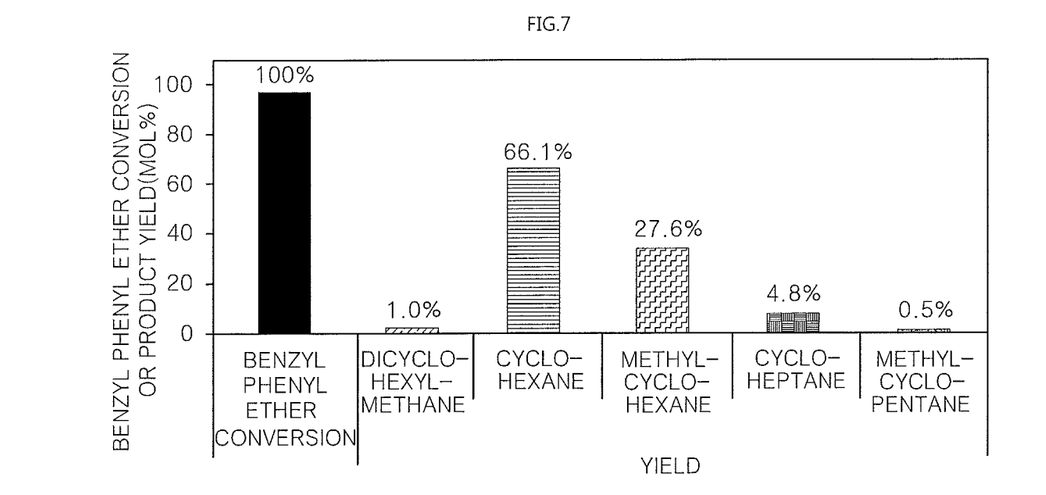
FIG. 7 is a graph illustrating the yields of the final products obtained from benzyl phenyl ether ($C_6H_5CH_2OC_6H_5$) via hydrodeoxygenation and byproducts according to Comparative Example 3.
Figure 8:
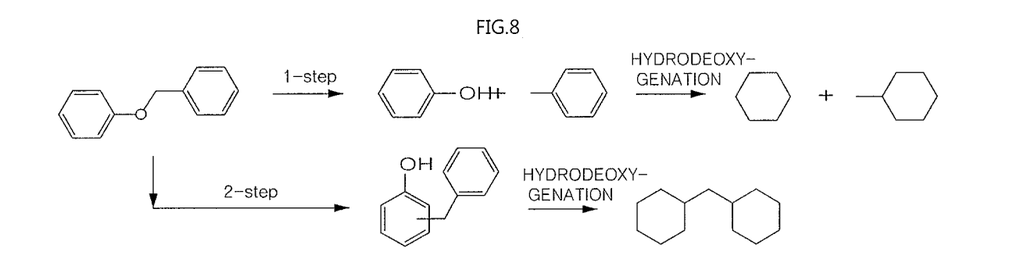
FIG. 8 shows comparison of Examples 1 and 2 with Comparative Example 3 in terms of the path through which the final products are obtained from benzyl phenyl ether ($C_6H_5CH_2OC_6H_5$).

Example 2 is repeated, except that isomerization is omitted. The results are shown in FIG. 7.

Test Example 1

Example 1 (FIG. 3), Comparative Example 1 (FIG. 4) and Comparative Example 2 (FIG. 5) are carried out by using a batch type reactor for a predetermined time, and then each product obtained after isomerization is analyzed for the comparison of composition.

As shown in FIG. 3, according to Example 1 in which a silicon-aluminum mixed oxide catalyst and hydrogen gas are introduced to the reactor to carry out isomerization, a conversion of benzyl phenyl ether ($C_6H_5CH_2OC_6H_5$) is 92.9 mol %, and 57.9 mol % of 2-benzylphenol (2-$C_6H_5CH_2C_6H_5OH$), 4.8 mol % of 4-benzylphenol (4-$C_6H_5CH_2C_6H_5OH$) and 10.8 mol % of phenol ($C_6H_5OH$) are provided.

As shown in FIG. 4, according to Comparative Example 1 in which no catalyst is introduced, a conversion of benzyl phenyl ether ($C_6H_5CH_2OC_6H_5$) is 0 mol %, and yield of 2-benzylphenol (2-$C_6H_5CH_2C_6H_5OH$), 4-benzylphenol (4-$C_6H_5CH_2C_6H_5OH$) and phenol ($C_6H_5OH$) is also 0, suggesting that no reaction occurs.

As shown in FIG. 5, according to Comparative Example 2 in which a silicon-aluminum mixed oxide catalyst and helium gas are introduced to the reactor to carry out isomerization, a conversion of benzyl phenyl ether ($C_6H_5CH_2OC_6H_5$) is 90.0 mol %, and 58.6 mol % of 2-benzylphenol (2-$C_6H_5CH_2C_6H_5OH$), 5.1 mol % of 4-benzylphenol (4-$C_6H_5CH_2C_6H_5OH$) and 10.5 mol % of phenol ($C_6H_5OH$) are provided.

It can be seen from the above results that a catalyst is required for isomerization, and that use of hydrogen gas and use of helium gas (a kind of inert gas) as a filling gas of the reactor provide a similar conversion of benzyl phenyl ether ($C_6H_5CH_2OC_6H_5$) and yields of intermediate products.

Test Example 2

Example 2 (FIG. 6) and Comparative Example 3 (FIG. 7) are carried out by using a batch type reactor for a predetermined time, and then each product obtained after hydrodeoxygenation is analyzed for the comparison of composition.

As shown in FIG. 6, according to Example 2 in which a rubidium/silicon-aluminum mixed oxide catalyst is used to perform hydrodeoxygenation of the intermediate products obtained from the isomerization of Example 1, a conversion of benzyl phenyl ether ($C_6H_5CH_2OC_6H_5$) is 100 mol %, and 58.7 mol % of dicyclohexylmethane ($C_6H_{11}CH_2C_6H_{11}$), 19.4 mol % of cyclohexane ($C_6H_{12}$), 3.1 mol % of methylcyclohexane ($C_6H_{11}CH_3$), and 18.9 mol % of a trimer (terpolymer of C18-C19 cycloalkanes) are provided.

On the contrary, as shown in FIG. 7, according to Comparative Example 3 in which isomerization is omitted, a conversion of benzyl phenyl ether ($C_6H_5CH_2OC_6H_5$) is 100 mol %, and 1.0 mol % of dicyclohexylmethane ($C_6H_{11}CH_2C_6H_{11}$), 66.1 mol % of cyclohexane ($C_6H_{12}$), 27.6 mol % of methylcyclohexane ($C_6H_{11}CH_3$), 4.8 mol % of cycloheptane ($C_7H_{14}$) and 0.5 mol % of methylcyclopentane ($C_5H_9CH_3$) are provided.

It can be seen from the above results that when isomerization is omitted (FIG. 7), the final reaction products are occupied mainly by cyclohexane ($C_6H_{12}$) and methylcyclohexane ($C_6H_{11}CH_3$) with a low carbon number due to the predominant cleavage of ether functional groups caused by the rubidium/silicon-aluminum mixed oxide catalyst. On the other hand, when carrying out hydrodeoxygenation after isomerization (FIG. 6), at least 80 mol % of the reaction products are occupied by 58.7 mol % of dicyclohexylmethane ($C_6H_{11}CH_2C_6H_{11}$) and 18.9 mol % of a trimer, which are compounds having the same carbon number as benzyl phenyl ether ($C_6H_5CH_2OC_6H_5$).

While the exemplary embodiments have been shown and described, it will be understood by those skilled in the art that various changes in form and details may be made thereto without departing from the spirit and scope of the present disclosure as defined by the appended claims.

What is claimed is:

1. A method for producing a high-carbon number saturated hydrocarbon using a biomass, comprising:
   introducing a mixed biomass solution containing benzyl phenyl ether ($C_6H_5CH_2OC_6H_5$) to a reactor and further introducing an acid catalyst or difunctional catalyst to the reactor to carry out isomerization of the mixed biomass solution to make an intermediate product; and
   carrying out hydrodeoxygenation of the intermediate product by introducing an acid catalyst or difunctional catalyst to the reactor together with hydrogen, after the isomerization, to induce hydrodeoxygenation of intermediate products obtained from the isomerization to produce the high-carbon number saturated hydrocarbon.

2. The method for producing a high-carbon number saturated hydrocarbon using a biomass according to claim 1, wherein the mixed biomass solution comprises the biomass containing benzyl phenyl ether, dissolved in at least one hydrocarbon solvent selected from the group consisting of pentane, hexane, heptane, octane, nonane, decane, undecane and dodecane.

3. The method for producing a high-carbon number saturated hydrocarbon using a biomass according to claim 1, wherein benzyl phenyl ether is present in the mixed biomass solution in an amount of 0.1-10 wt % based on the total weight of the solution.

4. The method for producing a high-carbon number saturated hydrocarbon using a biomass according to claim 1, wherein the acid catalyst includes a porous or non-porous carrier having acidic functional groups on the surface thereof.

5. The method for producing a high-carbon number saturated hydrocarbon using a biomass according to claim 4, wherein the carrier of the acid catalyst is at least one selected from the group consisting of aluminum, silicon and silicon-aluminum mixed oxide.

6. The method for producing a high-carbon number saturated hydrocarbon using a biomass according to claim 5, wherein the carrier of the acid catalyst is silicon-aluminum mixed oxide, and the atomic ratio of aluminum/(silicon+aluminum) in the composite oxide is 0.1-100.

7. The method for producing a high-carbon number saturated hydrocarbon using a biomass according to claim 4, wherein the acid catalyst has at least one shape selected from the group consisting of bulk, plates, powder, pellets, balls and aerogel.

8. The method for producing a high-carbon number saturated hydrocarbon using a biomass according to claim 1, wherein the metal catalyst contained in the difunctional catalyst is a metal nanoparticle catalyst.

9. The method for producing a high-carbon number saturated hydrocarbon using a biomass according to claim 8, wherein the metal is at least one metal selected from the group consisting of platinum, palladium, rubidium, iridium and rhodium or alloy thereof.

10. The method for producing a high-carbon number saturated hydrocarbon using a biomass according to claim 1, wherein the metal catalyst contained in the difunctional catalyst is supported in an amount of 0.1-20 wt % based on the weight of the carrier.

11. The method for producing a high-carbon number saturated hydrocarbon using a biomass according to claim 1, wherein the reactor is maintained at a temperature of 50-150° C. during the isomerization.

12. The method for producing a high-carbon number saturated hydrocarbon using a biomass according to claim 1, wherein the reactor is maintained at a temperature of 200-300° C. during the hydrodeoxygenation.

* * * * *